United States Patent
Yang

(10) Patent No.: US 10,201,471 B2
(45) Date of Patent: Feb. 12, 2019

(54) MASSAGE DEVICE

(71) Applicant: Cheng-Chuan Yang, Taichung (TW)

(72) Inventor: Cheng-Chuan Yang, Taichung (TW)

( * ) Notice: Subject to any disclaimer, the term of this patent is extended or adjusted under 35 U.S.C. 154(b) by 972 days.

(21) Appl. No.: 14/687,915

(22) Filed: Apr. 16, 2015

(65) Prior Publication Data

US 2016/0302963 A1 Oct. 20, 2016

(51) Int. Cl.
| | |
|---|---|
| *A61H 23/02* | (2006.01) |
| *A61F 7/02* | (2006.01) |
| *A61F 7/00* | (2006.01) |
| *A61H 23/00* | (2006.01) |
| *A61H 35/02* | (2006.01) |

(Continued)

(52) U.S. Cl.
CPC .............. *A61H 23/02* (2013.01); *A61F 7/007* (2013.01); *A61F 7/0085* (2013.01); *A61F 7/02* (2013.01); *A61H 5/00* (2013.01); *A61H 9/00* (2013.01); *A61H 23/00* (2013.01); *A61H 35/02* (2013.01); *A61F 2007/0003* (2013.01); *A61F 2007/0004* (2013.01); *A61F 2007/0054* (2013.01); *A61F 2007/0075* (2013.01); *A61F 2007/0076* (2013.01); *A61F 2007/0086* (2013.01); *A61H 9/0028* (2013.01); *A61H 2201/0207* (2013.01); *A61H 2201/0214* (2013.01); *A61H 2201/0242* (2013.01); *A61H 2201/0285* (2013.01); *A61H 2201/1604* (2013.01); *A61H 2201/5012* (2013.01); *A61H 2201/5097* (2013.01);

(Continued)

(58) Field of Classification Search
CPC ... A61H 7/00; A61H 5/00; A61H 9/00; A61H 35/02; A61H 23/00; A61H 23/02; A61H 2201/02; A61H 2201/0207; A61H 2201/0214; A61H 2201/0221; A61H 2201/0242; A61H 2201/0264; A61H 2201/0285; A61H 2205/024; A61F 7/00; A61F 7/0085; A61F 7/02; A61F 7/10; A61F 7/103; A61F 7/007; A61F 2007/0001; A61F 2007/0003; A61F 2007/0004; A61F 2007/0007; A61F 2007/0059; A61F 2007/0063; A61F 2007/0075; A61F 2007/0225; A61F 2007/0228

See application file for complete search history.

(56) References Cited

U.S. PATENT DOCUMENTS

| | | | | |
|---|---|---|---|---|
| 5,643,336 | A * | 7/1997 | Lopez-Claros | ........... A61F 7/02 126/204 |
| 6,155,995 | A * | 12/2000 | Lin | ........................ A61F 7/02 601/148 |

(Continued)

*Primary Examiner* — Colin W Stuart
(74) *Attorney, Agent, or Firm* — Rosenberg, Klein & Lee

(57) ABSTRACT

A massage device includes a hot and cold compress member that is connected to a circulating water tank via a connection pipe. An accommodating body is located between a water bag and a main body, and includes a heat conducting member, a cooling member and a heat dissipating member. The circulating water tank is connected to a control body which controls the operation of the heat conducting member, a cooling member. Water circulates through the water bag by a first pipe and a first pump, and the temperature of the water is controlled to provide appropriate temperature to enhance blood circulation of the users. The water bag is fastened to the accommodating body without using screws or bolts to avoid from being rusted and leakage.

5 Claims, 12 Drawing Sheets

(51) Int. Cl.
*A61H 9/00* (2006.01)
*A61H 5/00* (2006.01)
(52) U.S. Cl.
CPC .. *A61H 2205/022* (2013.01); *A61H 2205/024* (2013.01); *A61H 2205/025* (2013.01)

(56) References Cited

U.S. PATENT DOCUMENTS

| | | | | |
|---|---|---|---|---|
| 7,637,878 | B2* | 12/2009 | Lin | A61H 23/0263 601/37 |
| 9,271,865 | B2* | 3/2016 | Yang | A61H 23/0263 |
| 2004/0059400 | A1* | 3/2004 | Lin | A61F 7/007 607/109 |
| 2004/0249427 | A1* | 12/2004 | Nabilsi | A61F 7/0085 607/104 |
| 2005/0131504 | A1* | 6/2005 | Kim | A61F 7/007 607/104 |
| 2011/0251532 | A1* | 10/2011 | Yang | A61H 23/0263 601/18 |

\* cited by examiner

MASSAGE DEVICE

BACKGROUND OF THE INVENTION

1. Field of the Invention

The present invention relates to a massage device, and especially relates to a device for providing hot compress and cold compress and achieving the effects of promoting blood circulation, protecting muscles or eyes, and relaxing human body and massage.

2. Description of Related Art

The electronic applications, such as computers, smart phones, and etc., have become daily necessities due to technology development. Lots of people are using computers or electronic devices (such as tablets and smart phones) for work, entertainment, search, read, and etc. Therefore, paper work is gradually replaced by electronic devices and smart phones.

The eyes are easy to be tired, dry, sore, and red due to the electronic devices with blue lights and small words while seeing them for a long time. Therefore, many eye protection products are developed. Besides the necessity of the eye protection is important, other portions of human body may be also pain due to overuse or collision. The massage device may be used for relaxing affecting regions with hot compress or cold compress. The descriptions of the massage device for eyes are only for example and other massage devices are omitted, but not limited thereto.

There are many massage devices for relaxing eyes in health care market. Please refer to TW patent no. M386892 (a first generation massage device disclosed by the applicant) and FIG. 1, a massage device is disclosed (the numerals hereafter are referenced to the patent M386892) and mainly comprises a strip 1 and hot and cold compress member 2 arranged at the strip 1. The compress member 2 may include a water bag 21, a heat conducting member 22, and a semiconductor cooling member 23. The water bag 21 is used for pasting on eyes of human. The water bag 21 has a connection hole 215 for providing the heat conducting member 22 to pass through. The semiconductor cooling member 23 is arranged on the heat conducting member 22. The compress member 2 may include a cooling assembly 27 arranged at the heat dissipating member 25. The cooling assembly 27 may include a stand 26 corresponding to a heat dissipating piece 251 and a fan 272 arranged with the stand 26 and used for cooling the heat dissipating piece 251.

The temperature of the above mentioned massage device is controlled to heat or cool the heat conducting member 22 through the semiconductor cooling member 23 and the temperature of water in the water bag 21 may be controlled by the heat conducting member 22 so as to achieve the effects of hot compress and cold compress and relax eyes. However, the design of the fan 272 only enhances the convection around the hot air and the cold air. It may limit the effect of heat dissipation. Therefore, a second generation massage device is developed (please reference to TW application no. 102119966 and shown as in FIGS. 2 and 3) and comprises a hot and cold compress member 1, a circulating water tank 2, and a strip 15.

The compress member 1 includes a water bag 11, a heat conducting member 12, a cooling member 13, and a heat dissipating member 14. One side of the water bag 11 may be pasted at eyes of human. The heat conducting member 12 may be assembled to the other side of the water bag 11 opposite to the side pasted on eyes. The cooling member 13 is assembled to one side of the heat conducting member 12 opposite to the side assembled the water bag 11. The heat dissipating member 14 is pasted at the cooling member 13 and the water bag 11 and arranged at the circulating water tank 2 for circulation.

The circulating water tank 2 has at least one temperature control unit 21 for cooling the temperature of liquid in the heat conducting member 14.

The strip 15 is connected with the compress member 1 and surrounded the head of human.

Accordingly, the temperature of the liquid in the heat conducting member 12 may be controlled through the cooling member 13 so that the water bag 11 has the effects of hot compress and cold compress to relax eyes. The cold water in the heat dissipating member 14 is regulated so that the heat may be transmitted between the heat dissipating member 14 and the cooling member 13 to quickly dissipate heat generated from the cooling member 13.

There are some drawbacks derived from the second generation massage device (shown as in FIGS. 2 to 4) and described as below.

Firstly, it is easy to be rusty and decrease thermal conductivity because the heat conducting member 12 is fastened in the water bag 11 by the fastening member 111 and the metal plate of the heat conducting member 12 is soaked in water of the water bag 11.

Secondly, it will be loosed and leakage because the fastening member 111 is soaked in water of the water bag 11 and then easy to be rusty so that the structure of the massage device is unstable and dangers will happen due to leakages of electricity or water.

Thirdly, the leakage of water is easily happened to the water bag 11 while the fastening member 111 is loosed because the water bag 11 is fastened on the heat conducting member 12 or heat conducting plate 18 and the water bag 11 is made by plastic materials.

Fourthly, no matter what the fastening member 111 is a screw for screwing tightly or used an adhesive to stick on, an interval or gap is formed due to difference in temperature and thermal expansion and contraction so that the water bag 11 made by plastic materials and the metal plate of the heat conducting member 12 or heat conducting plate 18 are hard to combine with each other.

Fifthly, heat is easy staying around the heat conducting plate 18 or the heat conducting member 12 and hard to be dissipated to other regions to balance temperature while heating or cooling water in the water bag 11 due to the heat conducting plate 18 or the heat conducting member 12 are arranged in a fixed position disposed in the water bag 11. It cannot hot compress or cold compress around eyes and the effects is also decreased.

Furthermore, please reference to FIG. 5 (please also reference to TW patent no. M485036), another kind of massage device is used for whole face of human, but it still has the drawbacks the same as the second generation massage device.

In view of the foregoing circumstances, the inventor has invested a lot of time to study the relevant knowledge, compare the pros and cons, research and develop related products. After quite many experiments and tests, the "massage device" of this invention is eventually launched to improve the foregoing shortcomings, to meet the public use.

SUMMARY OF THE INVENTION

In order to improve above mentioned drawbacks, a massage device is provided. The massage device may comprise a hot and cold compress member and a circulating water tank, wherein:

the compress member includes a main body, an accommodating body, a water bag, and a fastening plate, a receiving space is formed inside the main body for receiving the accommodating body, the water bag, and the fastening plate;

a plurality of accommodating portions are formed at one side of the accommodating body, and a pasting portion is arranged at the other side of the accommodating body opposite to the side formed the accommodating portions, the pasting portion is provided for pasting at a location which needs compress, a plurality of fastening holes are formed at peripheral of the accommodating body, and a heat conducting member, a cooling member, and a hot dissipating member are received at corresponding accommodating portion in order;

the heat conducting member is made by a heat conductive material, the cooling member is a thermoelectric cooling chip for controlling to heat or cool the heat conducting member, the heat dissipating member is for dissipating heat of the cooling member, and the accommodating body is fastened in the receiving space of the main body by a fastening member;

a first circulating pump is further arranged and fastened on one of the accommodating portions of the accommodating body;

the water bag is a bag with a close space and pasted on the pasting portion of the accommodating body;

a first circulating pipe is further arranged and fluidly communicated with the water bag, the first circulating pump, and the heat conducting member in series so as to balance temperature of water in the water bag;

the fastening plate is a ring member with a pasting hole corresponding to the shape of the water bag, and a plurality of fastening portions are formed at peripheral of the ring member corresponding to the shapes and locations of the fastening holes so that the water bag is fastened on the pasting portion of the accommodating body while the fastening portions of the fastening plate is fastened in the fastening holes of the accommodating body;

the circulating water tank includes a control body and a vessel body, the control body and the vessel body are integrated together by lock, and a cavity is formed in the vessel body for receiving water;

the control body includes a control interface and a second circulating pump, the control interface is electrically connected with a control circuit, the control circuit is also electrically connected to the cooling member, the first circulating pump, and the second circulating pump so that the operations of the cooling member, the first circulating pump, and the second circulating pump are controlled by the control interface to achieve the effect of controlling and modifying operations; and a second circulating pipe is further arranged to be fluidly communicated with the second circulating pump and heat dissipating member in series so that water in the cavity of the vessel body is flowed and circulated to make the heat dissipating member quickly dissipate heat.

In some embodiments, the control interface is wiredly or wirelessly electrically connected with the control circuit.

In some embodiments, the massage device further comprises a vibrating motor arranged at the accommodating body corresponding to a pasting part of the water bag, the vibrating motor is electrically connected to the control circuit and controlled by the control interface so that the effect of massage is achieved by vibration generated from the vibrating motor.

In some embodiments, the massage device further comprises a strip, two hook portions are respectively arranged at two ends of the strip, and two button holes are respectively arranged at two sides of the compress member so that the strip is tightly covered at the head of a user by buckling the hook portions to corresponding button holes.

In some embodiments, the massage device further comprises a connection pipe for connecting the compress member and circulating water tank, and a space defined inside the connection pipe is provided for receiving wires electrically connected to the control circuit to protect wires.

The various objectives and advantages of the present invention will be more readily understood from the following detailed description when read in conjunction with the appended drawing.

DETAILED DESCRIPTION OF THE INVENTION

To describe clearly that the present invention achieves the foregoing objective and function, the technical features and desired function are described with reference to a preferred embodiment and accompanying drawings.

Figure 1:
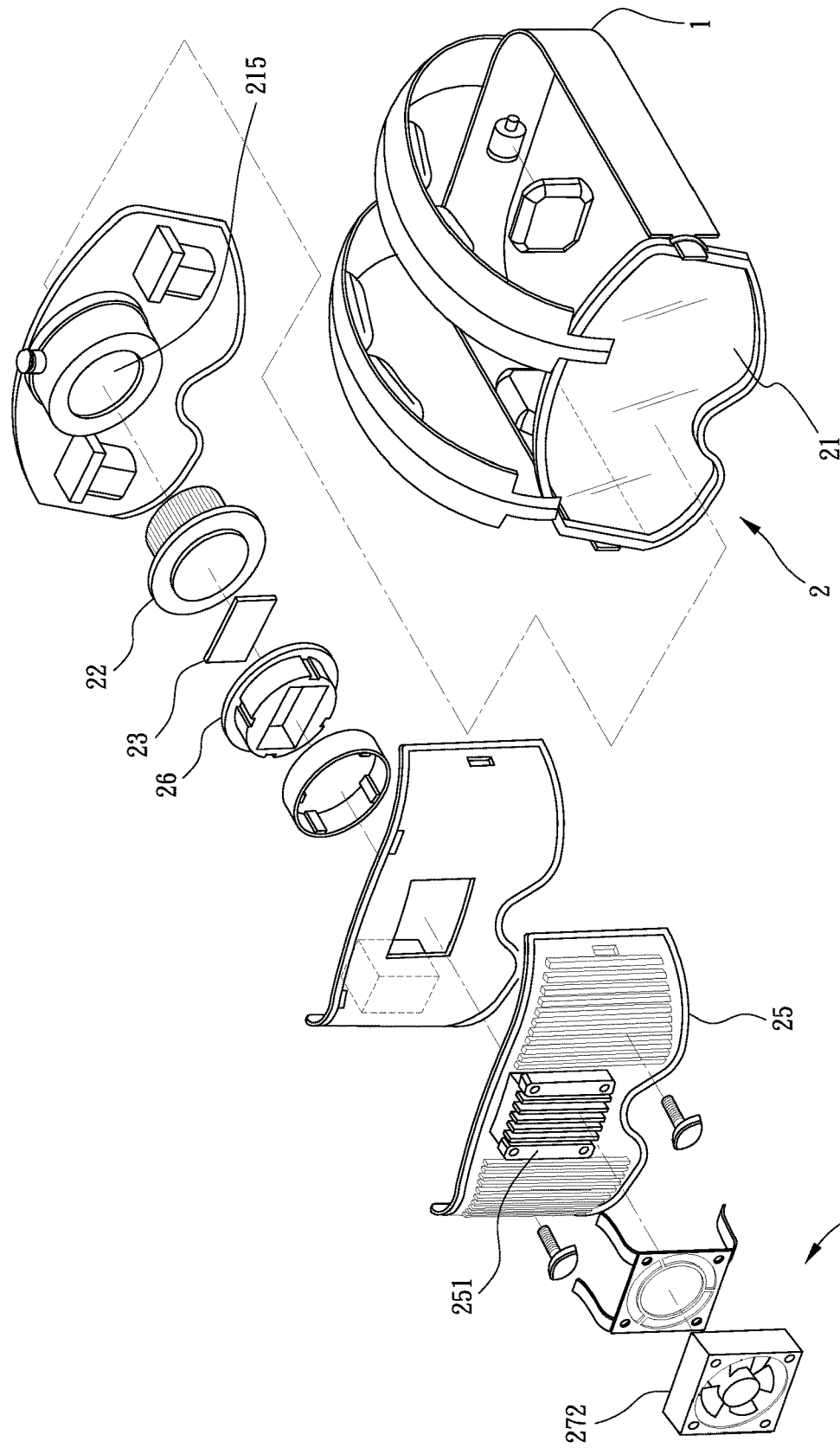
FIG. 1 is a perspective view of a conventional first generation massage device.
Figure 2:
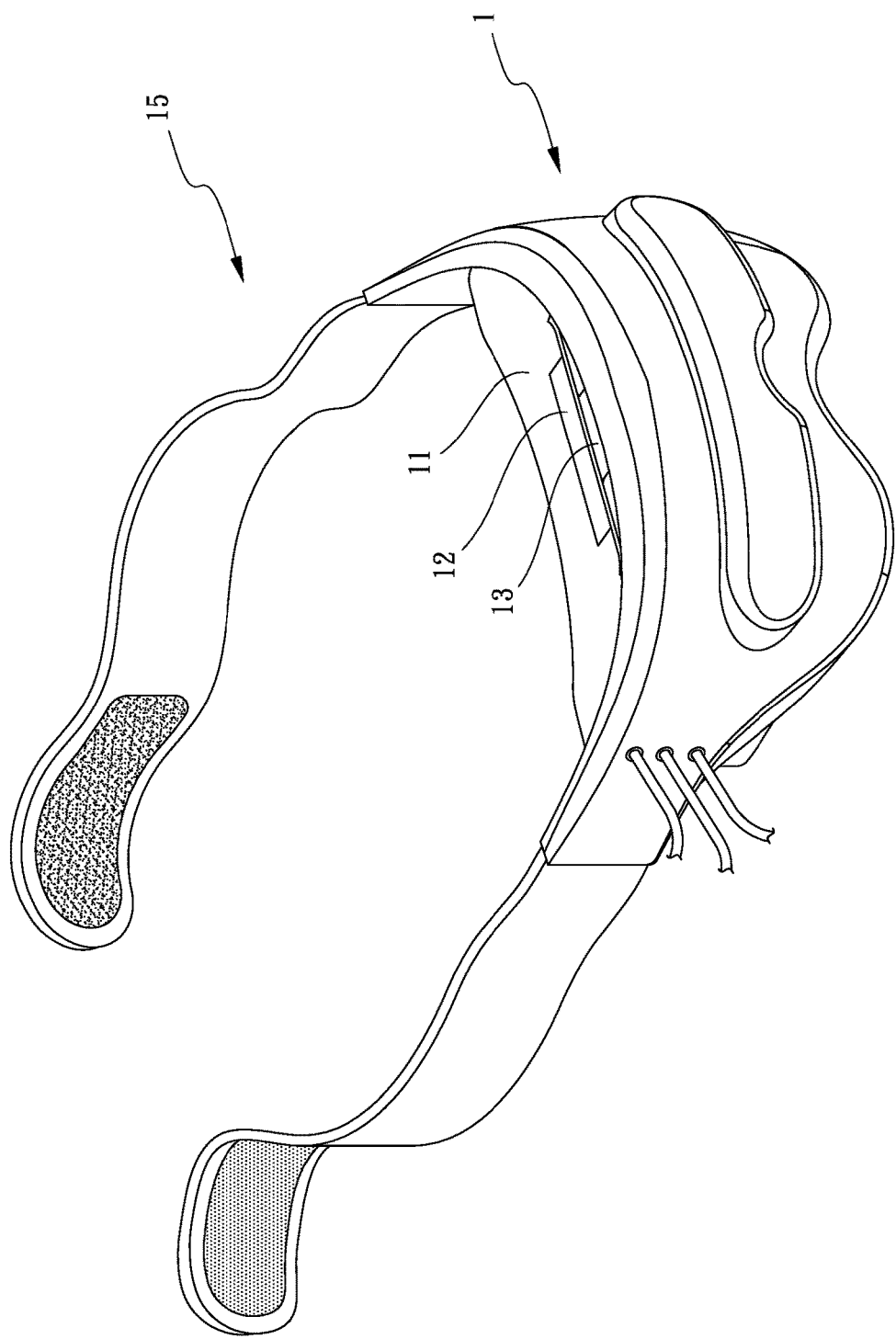
FIG. 2 is a perspective view of a conventional second generation massage device.
Figure 3:
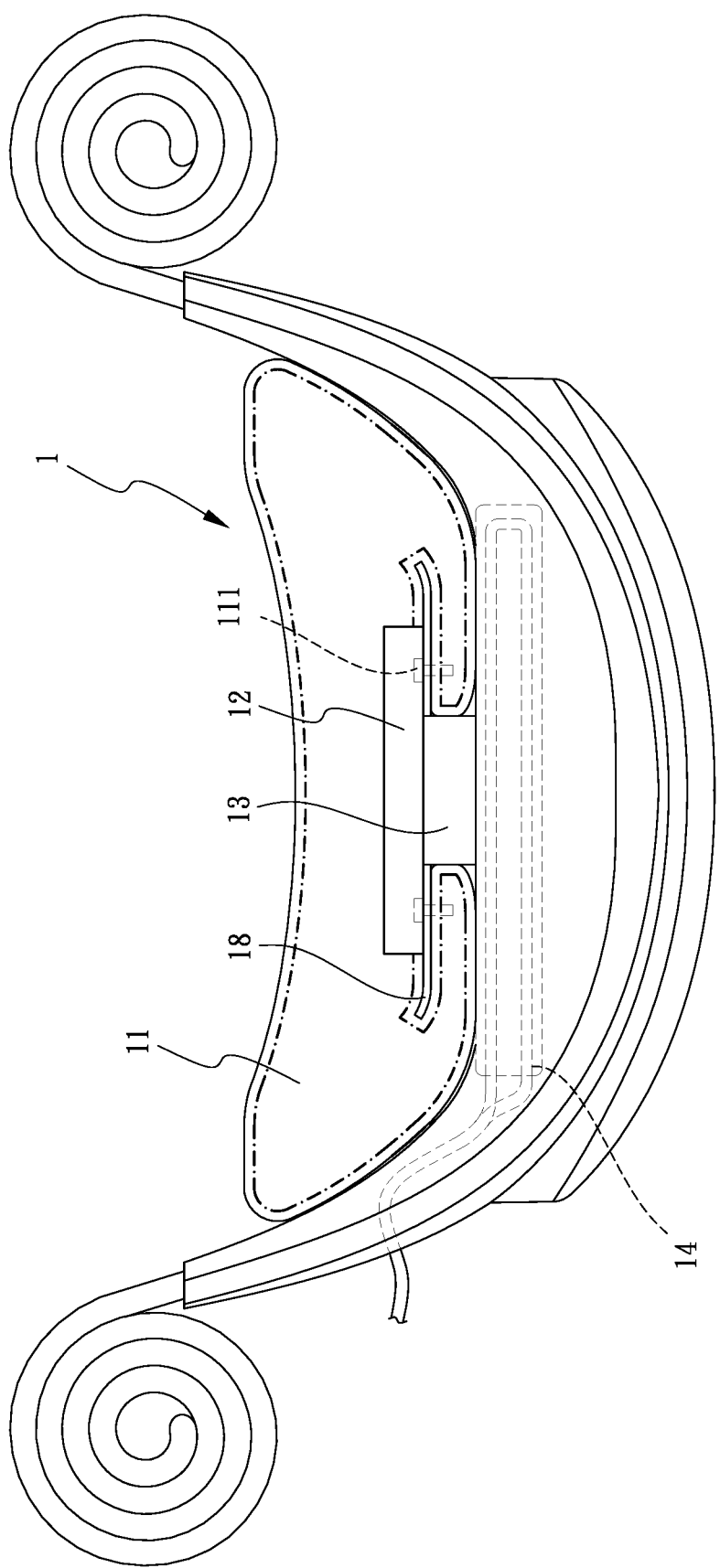
FIG. 3 is a cross-sectional view of FIG. 2.
Figure 4:
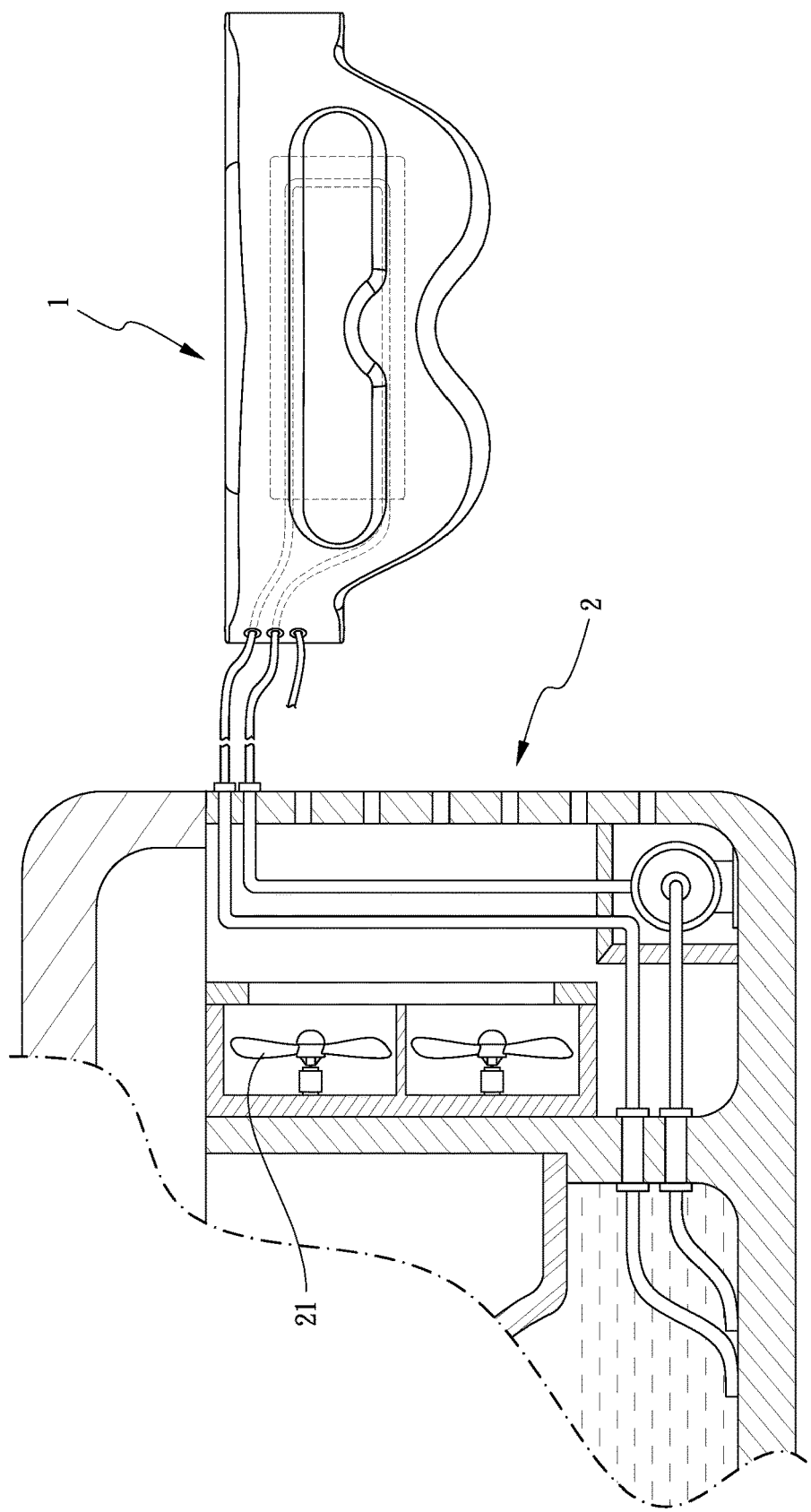
FIG. 4 is another cross-sectional view of FIG. 2.
Figure 5:
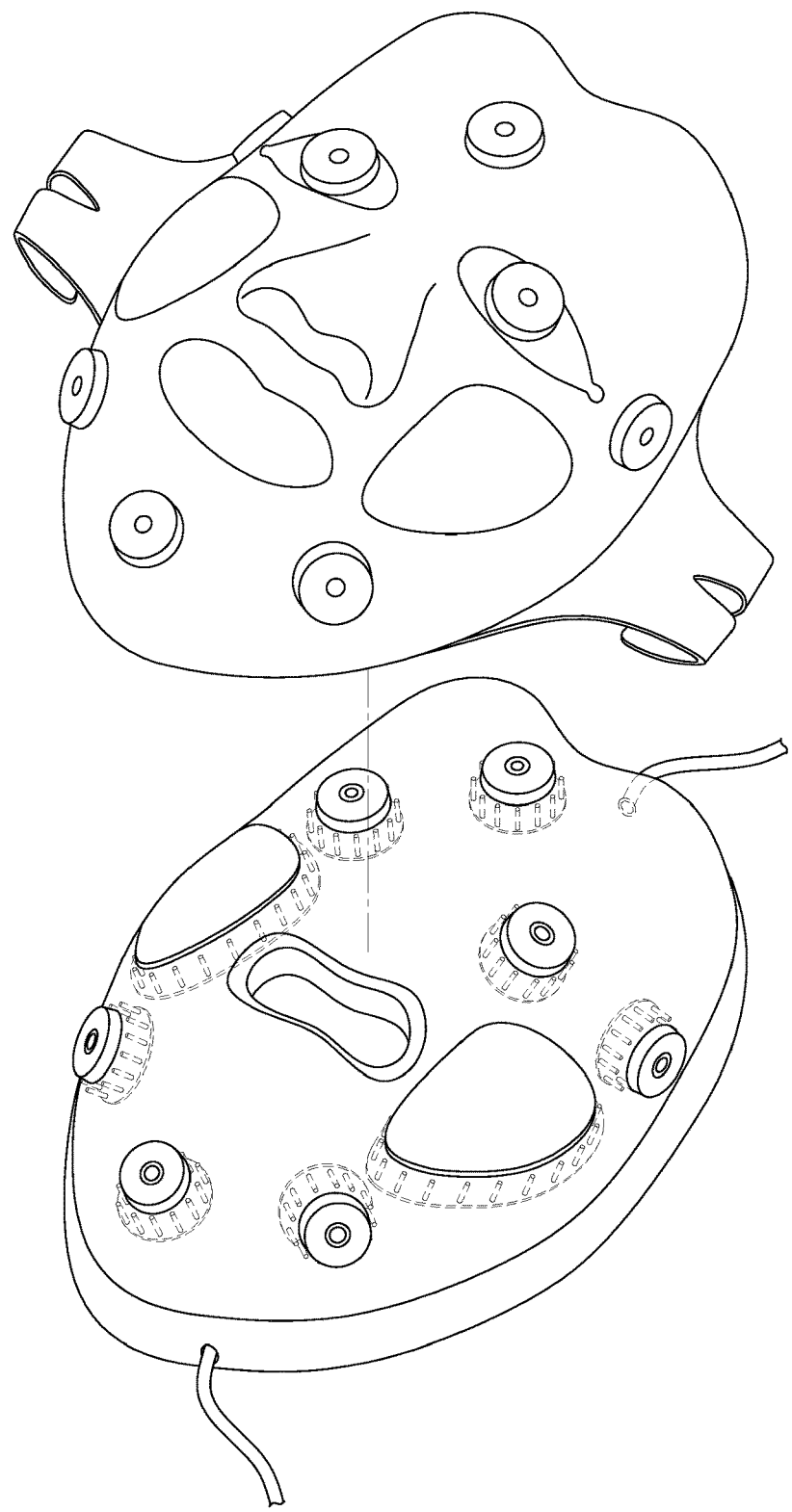
FIG. 5 is a perspective view of a conventional third generation massage device of the present invention.
Figure 6:
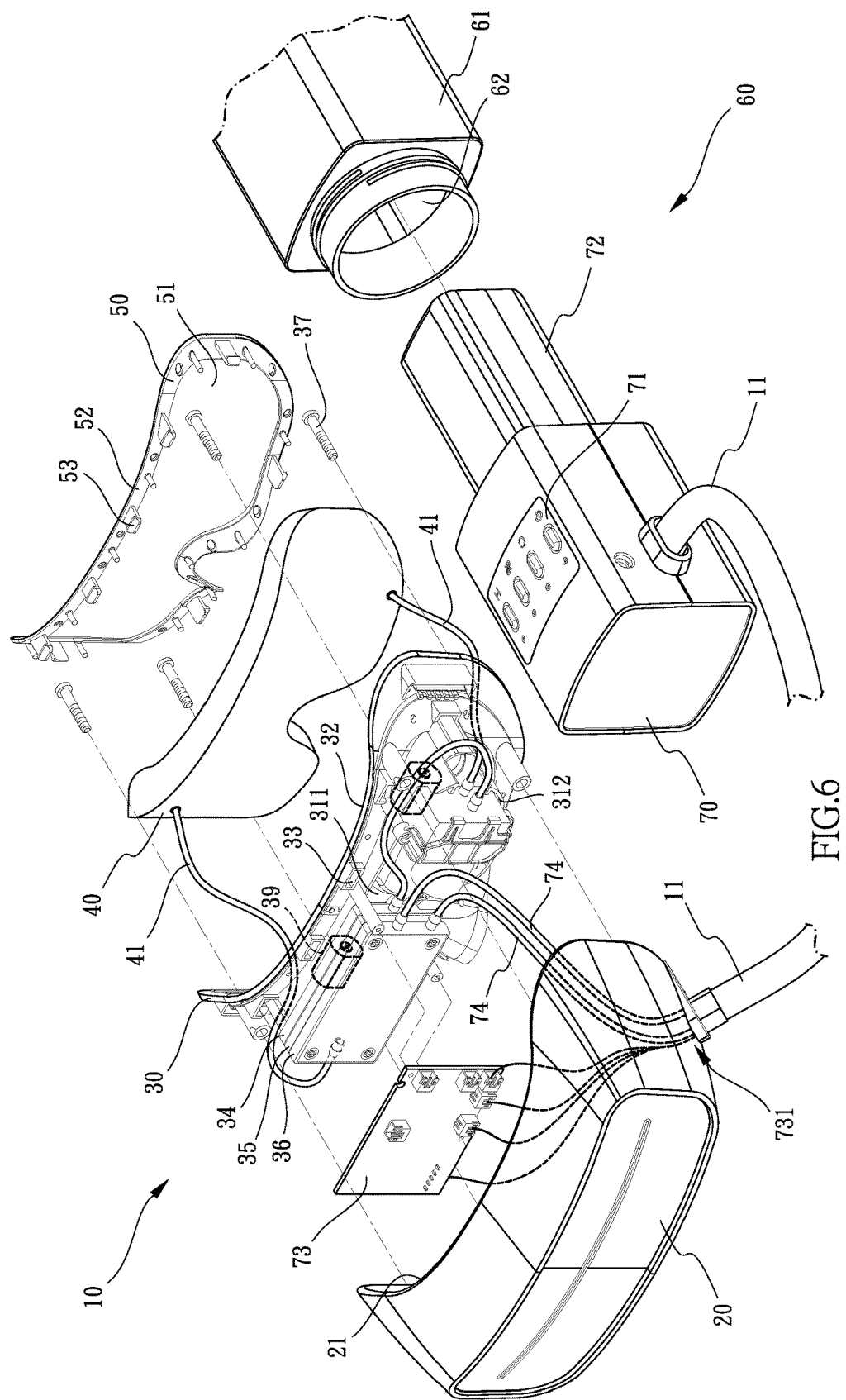
FIG. 6 is an exploded view of a massage device of the present invention.
Figure 7:
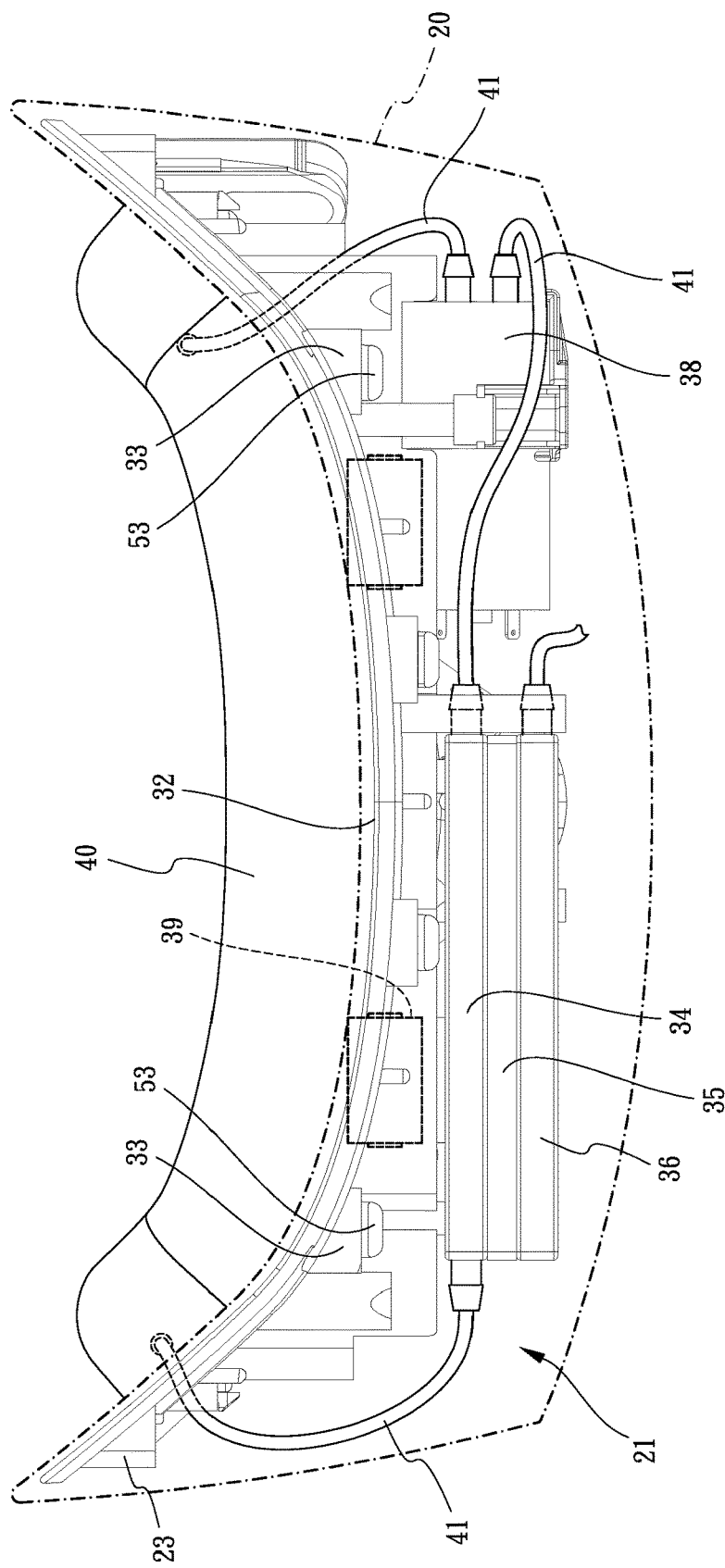
FIG. 7 is a cross-sectional view of the massage device of the present invention.

Please reference to FIGS. 6 and 7, the present invention relates to a massage device (it is illustrated that the eye massage is for example, but not limited thereto). The massage device mainly comprises a hot and cold compress member 10 and a circulating water tank 60. The compress member 10 may be connected to the circulating water tank 60 with a connection pipe 11.

The compress member 10 includes a main body 20, an accommodating body 30, a water bag 40, and a fastening plate 50. A receiving space 21 is formed inside the main body 20 for receiving the accommodating body 30, the water bag 40, and the fastening plate 50.

A plurality of accommodating portions 311 and 312 are formed at one side of the accommodating body 30, and a pasting portion 32 is arranged at the other side of the accommodating body 30 opposite to the side formed the accommodating portions 311 and 312. The pasting portion 32 is provided for pasting at a location which needs compress. A plurality of fastening holes 33 are formed at peripheral of the accommodating body 30. A heat conducting member 34, a cooling member 35, and a hot dissipating member 36 are received at corresponding accommodating portion 311 in order.

The heat conducting member 34 is made by a heat conductive material. The cooling member 35 is a thermoelectric cooling chip for controlling to heat or cool the heat conducting member 34. The heat dissipating member 36 is for dissipating heat of the cooling member 35 (shown as in FIG. 7). And the accommodating body 30 is fastened in the receiving space 21 of the main body 20 by a fastening member 37.

A first circulating pump 38 is further arranged and fastened on one of the accommodating portions 312 of the accommodating body 30.

The water bag 40 is a bag with a closed space and pasted on the pasting portion 32 of the accommodating body 30. The shape of the water bag 40 is corresponding to the location of wanting to be compressed and the illustration of eye shape is for example.

A first circulating pipe 41 is further arranged and fluidly communicated with the water bag 40, the first circulating pump 38, and the heat conducting member 34 in series (shown as in FIGS. 6 and 7) so that water in the water bag 40 is forced by the first circulating pump 38 and circulated among the water bag 40, the first circulating pump 38, and the heat conducting member 34 through the fluid communication of the first circulating pipe 41 to balance temperature of water in the water bag 40 and evenly transmitted to the location of wanting to be compressed.

Figure 11:
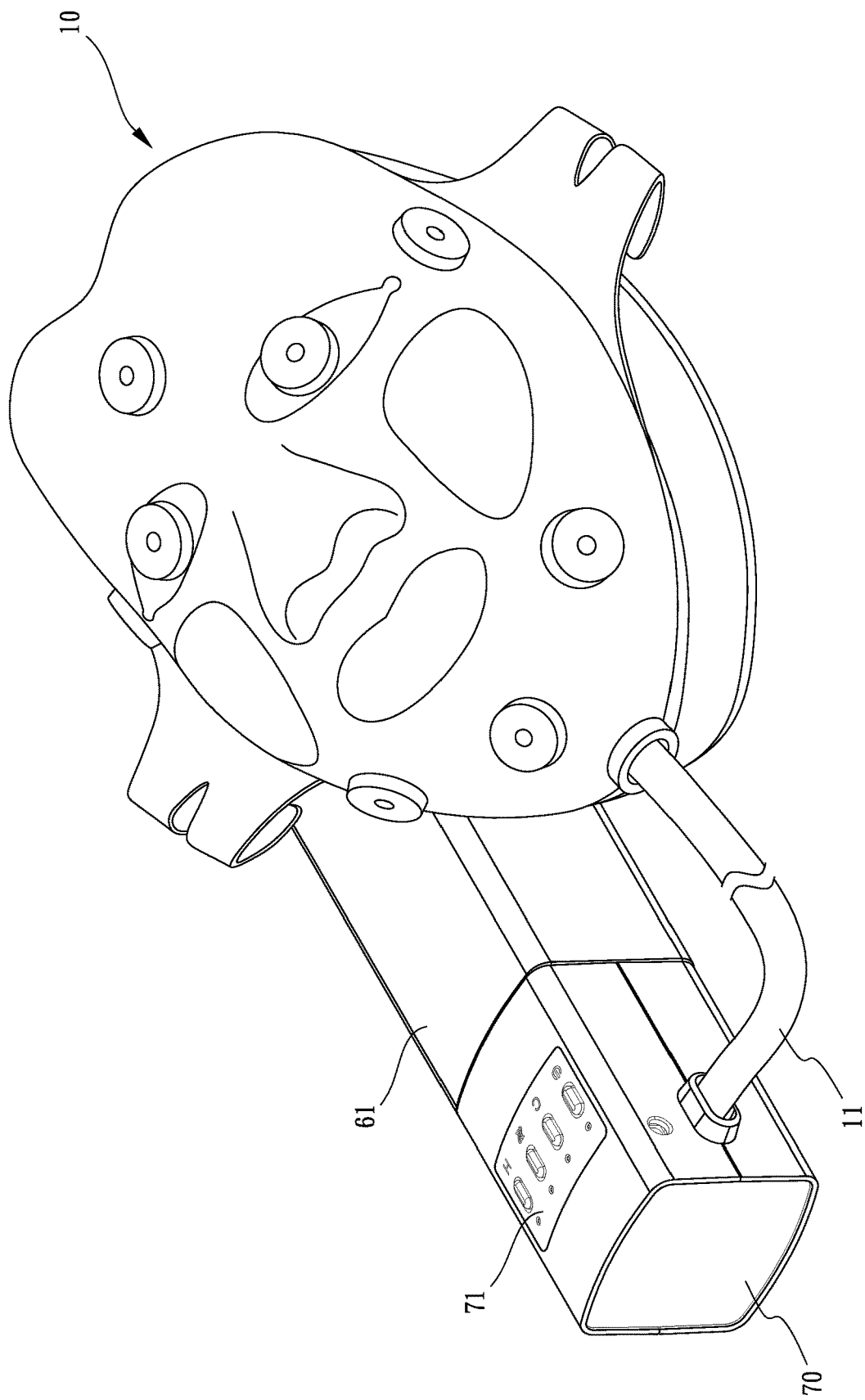
FIG. 11 is an exploded view of the massage device of the present invention applied to the face of a user.
Figure 12:
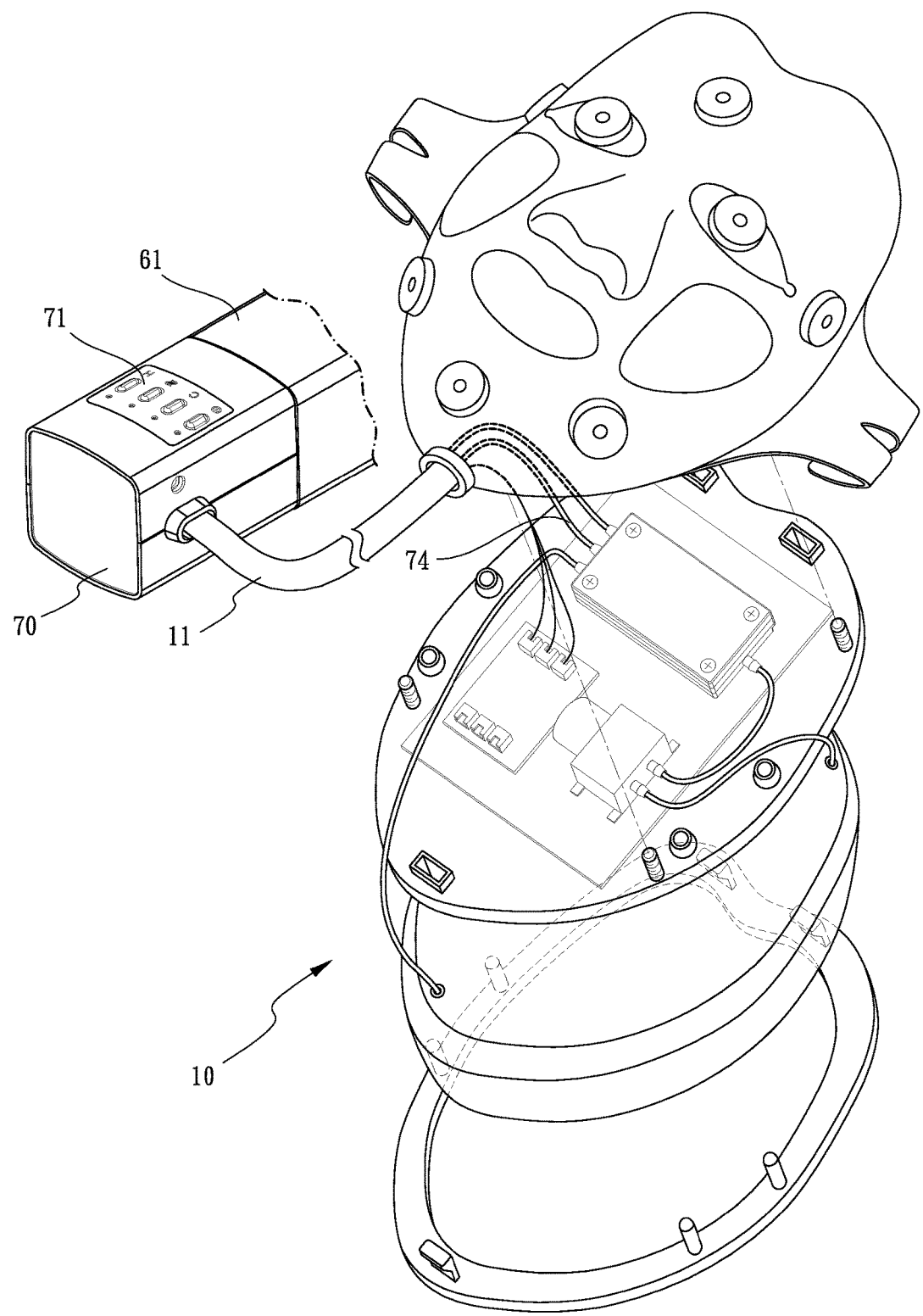
FIG. 12 is a perspective view of the massage device of the present invention applied to the face of the user.

The fastening plate 50 is a ring member with a pasting hole 51 corresponding to the shape of the water bag 40. And a plurality of fastening portions 53 are formed at peripheral 52 of the ring member corresponding to the shapes and locations of the fastening holes 33 of the accommodating body 30 so that the water bag 40 is fastened on the pasting portion 32 of the accommodating body 30 while the fastening portions 53 of the fastening plate 50 is fastened in the fastening holes 33 of the accommodating body 30. The main body 20, the accommodating body 30, the water bag 40, and the fastening plate 50 may be integrated in one device (shown as in FIG. 11).

Figure 8:
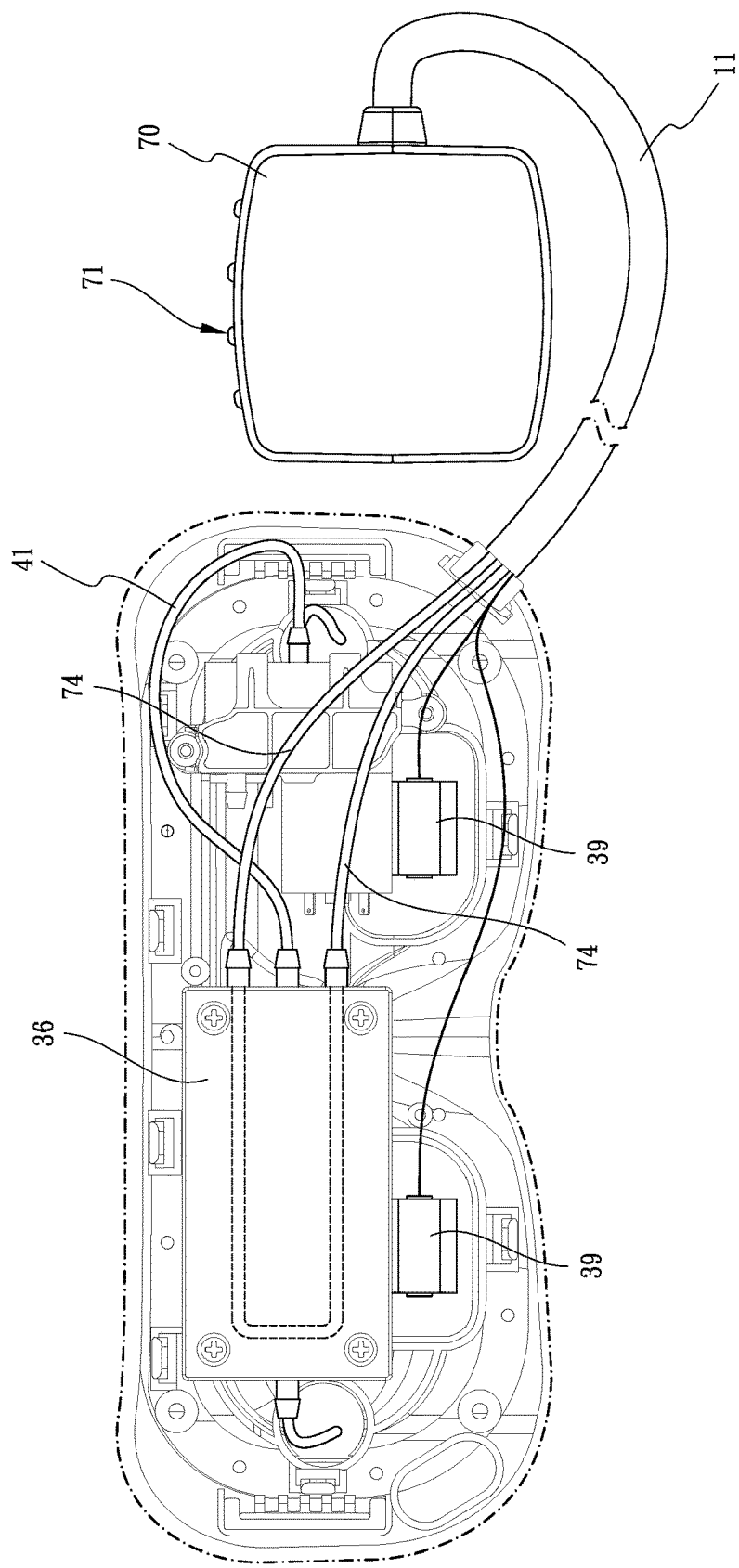
FIG. 8 is another cross-sectional view of the massage device of the present invention.

The circulating water tank 60 includes a control body 70 and a vessel body 61 (shown as in FIGS. 6 and 8). The control body 70 and the vessel body 61 are integrated together by lock. And a cavity 62 is formed in the vessel body 61 for receiving water. The control body 70 includes a control interface 71 and a second circulating pump 72. The control interface 71 is electrically connected with a control circuit 73 (wiredly or wirelessly). The control circuit 73 is also electrically connected to the cooling member 35, the first circulating pump 38, and the second circulating pump 72 so that the operations of the cooling member 35, the first circulating pump 38, and the second circulating pump 72 are controlled by the control interface 71 to achieve the effect of controlling and modifying operations.

A second circulating pipe 74 is further arranged to be fluidly communicated with the second circulating pump 72 and heat dissipating member 36 in series (shown as in FIGS. 8 and 9) so that water in the cavity 62 of the vessel body 61 is forced by the second circulating pump 72 and flowed among the circulating water tank 60, the second circulating pump 72, and heat dissipating member 36 through fluid communication of the second circulating pipe 74 and circulated to make the heat dissipating member quickly dissipate heat (that is, the heat of the cooling member 35 is quickly transmitted to the heat dissipating member 36 through the second circulating pipe 74 to keep the effects generated from the cooling member 35 or the heat conducting member 34).

The advantage of this invention is that water in the water bag 40 is forced by the first circulating pump 38 and flowed among the water bag 40, the first circulating pump 38, and the heat conducting member 34 through the fluid communication of the first circulating pipe 41, and further water with higher temperature adjacent to the heat conducting member 34 is circulated to the water bag 40 due to circulating flow of water so as to balance the temperature of water. And the heat conducting member 34 is not arranged in the water bag 40 so as to prevent from rustiness, leakage, and unstable structure.

In addition, water in the cavity 62 of the vessel body 61 of the circulating water tank 60 is forced by the second pump 72 and flowed among the circulating water tank 60, the second circulating pump 72, and the heat dissipating member 36 through the fluid communication of the second circulating pipe 74 and the heat generated from the cooling member 35 is quickly dissipated by the heat dissipating member 36 due to circulating flow of water to keep the affects generated from the cooling member 35 or the heat conducting member 34.

The above mentioned circulation manners may achieve the effect of balancing temperature and quickly dissipating heat through the heat dissipating member 36.

Because the water bag 40 is fastened on the pasting portion 32 of the accommodating body 30 while the fastening portions 53 of the fastening plate 50 is fastened in the fastening holes 33 of the accommodating body 30, the main body 20, the accommodating body 30, the water bag 40, and the fastening plate 50 are integrated in one device. Therefore, there is no metal material or metal fastening member for being fastened and then there is no problem of rustiness or leakage. And there is no unstable structure happened, either.

Figure 9:
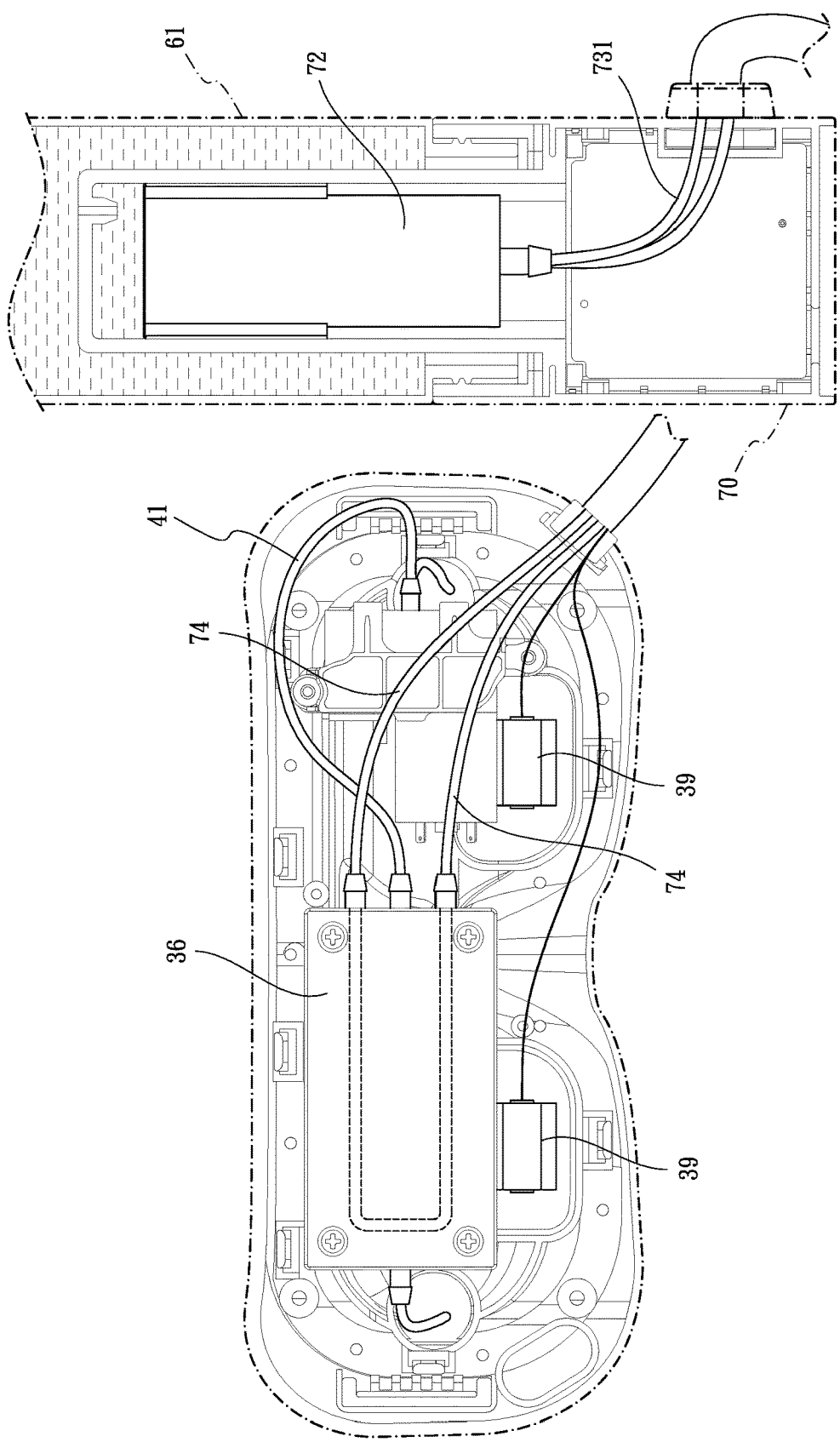
FIG. 9 is a cross-sectional view of a circulating water tank of the massage device of the present invention.

Please refer to FIGS. 6 and 9, the massage device further comprises two vibrating motors 39, which is arranged at the accommodating body 30 corresponding to a pasting part of the water bag 40. The vibrating motors 39 are electrically connected to the control circuit 73 and controlled by the control interface 71 so that the effect of massage is achieved by vibration generated from the vibrating motors 39.

Figure 10:
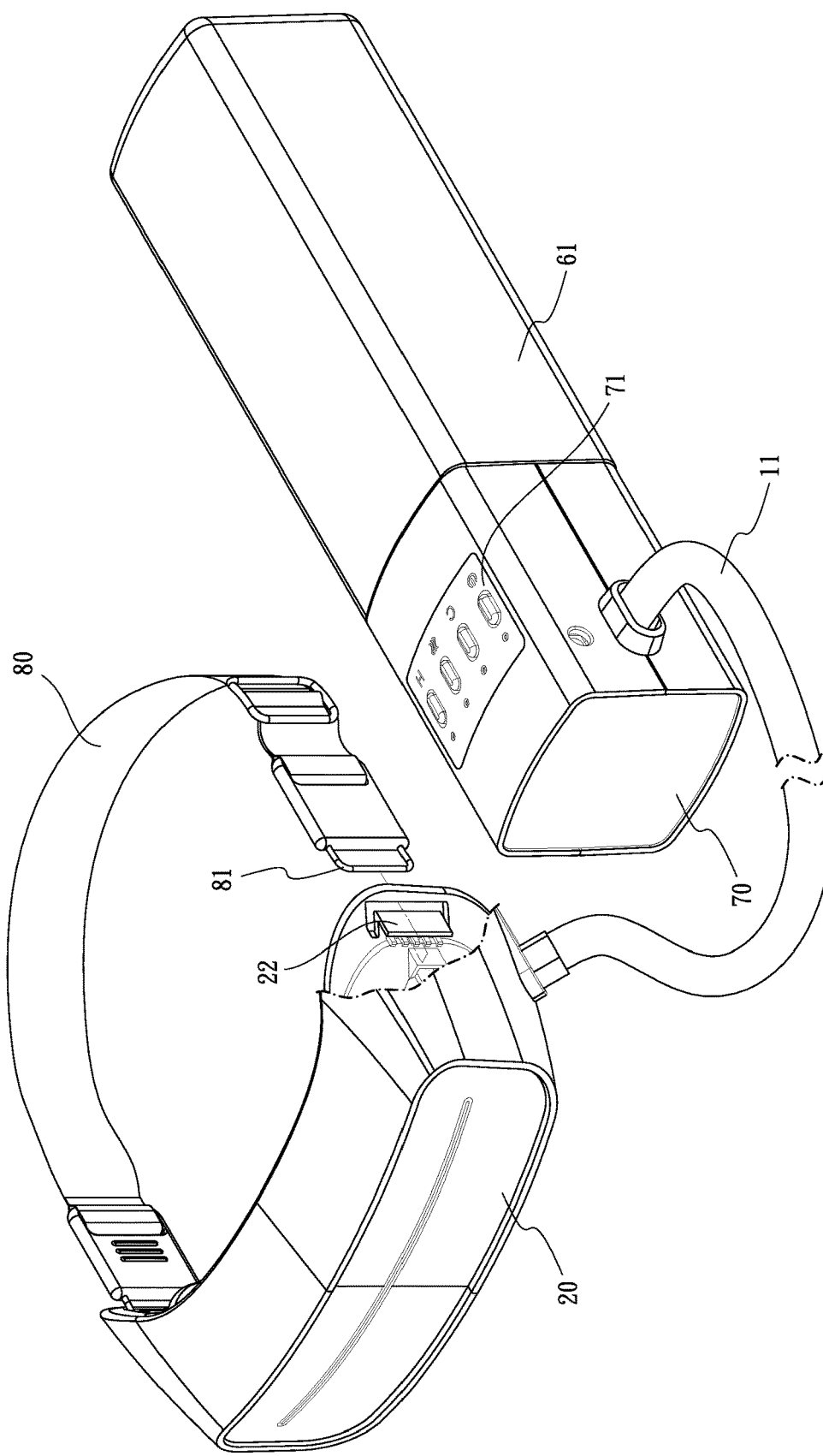
FIG. 10 is a perspective view of the massage device of the present invention after assembling.

Furthermore, please refer to FIG. 10, the massage device further comprises a strip 80. Two hook portions 81 are respectively arranged at two ends of the strip 80, and two button holes 22 are respectively arranged at two sides of the main body 20 of the compress member 10 so that the strip 80 may be tightly covered at the head of a user by buckling the hook portions 81 to corresponding button holes 22.

Besides, the massage device further comprises a connection pipe 11 for connecting the compress member 10 and circulating water tank 60. And a space defined inside the connection pipe 11 may be provided for receiving wires 731 electrically connected to the control circuit 73 to protect wires 731.

The foregoing descriptions are merely the exemplified embodiments of the present invention, where the scope of the claim of the present invention is not intended to be limited by the embodiments. Any equivalent embodiments or modifications without departing from the spirit and scope of the present invention are therefore intended to be embraced.

The disclosed structure of the invention has not appeared in the prior art and features efficacy better than the prior structure which is construed to be a novel and creative invention, thereby filing the present application herein subject to the patent law.

What is claimed is:

1. A massage device, comprising a hot and cold compress member and a circulating water tank, wherein:

the hot and cold compress member includes a main body, an accommodating body, a water bag, and a fastening plate, a receiving space is formed inside the main body for receiving the accommodating body, the water bag, and the fastening plate;

a plurality of accommodating portions are formed at one side of the accommodating body, and a pasting portion is arranged at the other side of the accommodating body opposite to the side forming the plurality of accommodating portions, the pasting portion is provided for pasting at a location which needs compress, a plurality of fastening holes are formed at a peripheral of the accommodating body, and a heat conducting member, a cooling member, and a heat dissipating member are received at an accommodating portion of the plurality of accommodating portions in order;

the heat conducting member is made by a heat conductive material, the cooling member is a thermoelectric cooling chip for controlling to heat or cool the heat conducting member, the heat dissipating member is for dissipating heat of the cooling member, and the accommodating body is fastened in the receiving space of the main body by a fastening member;

a first circulating pump is further arranged and fastened on one of the accommodating portions of the accommodating body;

the water bag is a bag with a closed space and pasted on the pasting portion of the accommodating body;

a first circulating pipe is further arranged and fluidly communicated with the water bag, the first circulating pump, and the heat conducting member in series so as to balance temperature of water in the water bag;

the fastening plate is a ring member with a pasting hole corresponding to the shape of the water bag, and a plurality of fastening portions are formed at a peripheral of the ring member corresponding to the shapes and locations of the plurality of fastening holes so that the water bag is fastened on the pasting portion of the accommodating body while the plurality of fastening portions of the fastening plate is fastened in the plurality of fastening holes of the accommodating body;

the circulating water tank includes a control body and a vessel body, the control body and the vessel body are integrated together by lock, and a cavity is formed in the vessel body for receiving water;

the control body includes a control interface and a second circulating pump, the control interface is electrically connected with a control circuit, the control circuit is also electrically connected to the cooling member, the first circulating pump, and the second circulating pump so that the operations of the cooling member, the first circulating pump, and the second circulating pump are controlled by the control interface to achieve the effect of controlling and modifying operations; and a second circulating pipe is further arranged to be fluidly communicated with the second circulating pump and heat dissipating member in series so that water in the cavity of the vessel body is flowed and circulated to make the heat dissipating member quickly dissipate heat.

2. The massage device as claimed in claim 1, wherein the control interface is wiredly or wirelessly electrically connected with the control circuit.

3. The massage device as claimed in claim 1, further comprises a vibrating motor arranged at the accommodating body corresponding to a pasting part of the water bag, the vibrating motor is electrically connected to the control circuit and controlled by the control interface so that the effect of massage is achieved by vibration generated from the vibrating motor.

4. The massage device as claimed in claim 1, further comprises a strip, two hook portions are respectively arranged at two ends of the strip, and two button holes are respectively arranged at two sides of the hot and cold compress member so that the strip is adapted to be tightly covered at the head of a user by buckling the hook portions to corresponding button holes.

5. The massage device as claimed in claim 1, further comprises a connection pipe for connecting the hot and cold compress member and circulating water tank, and a space defined inside the connection pipe is provided for receiving wires electrically connected to the control circuit to protect wires.

* * * * *